(12) United States Patent
Ben Nun

(10) Patent No.: US 7,815,678 B2
(45) Date of Patent: Oct. 19, 2010

(54) ACCOMMODATING INTRAOCULAR LENS (AIOL), AND AIOL ASSEMBLIES INCLUDING SAME

(75) Inventor: Yehoshua Ben Nun, D. N. Vitkin (IL)

(73) Assignee: NuLens Ltd., Herzliya Pituach (IL)

( * ) Notice: Subject to any disclaimer, the term of this patent is extended or adjusted under 35 U.S.C. 154(b) by 557 days.

(21) Appl. No.: 11/577,293

(22) PCT Filed: Oct. 9, 2005

(86) PCT No.: PCT/IL2005/001069

§ 371 (c)(1),
(2), (4) Date: Apr. 19, 2007

(87) PCT Pub. No.: WO2006/040759

PCT Pub. Date: Apr. 20, 2006

(65) Prior Publication Data

US 2007/0244561 A1 Oct. 18, 2007

Related U.S. Application Data

(60) Provisional application No. 60/617,738, filed on Oct. 13, 2004.

(51) Int. Cl.
*A61F 2/16* (2006.01)

(52) U.S. Cl. .................... 623/6.37; 623/6.13; 623/6.22

(58) Field of Classification Search ................ 623/6.11, 623/6.13, 6.22, 6.27, 6.37
See application file for complete search history.

(56) References Cited

U.S. PATENT DOCUMENTS

| | | | |
|---|---|---|---|
| 3,950,082 A | 4/1976 | Volk | |
| 4,122,556 A | 10/1978 | Poler | |
| 4,254,509 A | 3/1981 | Tennant | |
| 4,298,994 A | 11/1981 | Clayman | |
| 4,340,979 A | 7/1982 | Kelman | |
| 4,409,690 A | 10/1983 | Gess | |
| 4,409,691 A | 10/1983 | Levy | |
| 4,445,998 A | 5/1984 | Kanda et al. | |
| 4,446,581 A | 5/1984 | Blake | |
| 4,494,254 A | 1/1985 | Lopez | |
| 4,530,117 A | 7/1985 | Kelman | |

(Continued)

FOREIGN PATENT DOCUMENTS

EP    0 156 472 A    10/1985

(Continued)

OTHER PUBLICATIONS

U.S. Appl. No. 11/568,416, Nun.

(Continued)

*Primary Examiner*—William H. Matthews
(74) *Attorney, Agent, or Firm*—Morgan, Lewis & Bockius, LLP

(57) ABSTRACT

An accommodating intraocular lens (AIOL) including a biasing mechanism for elastically deforming an elastically deformable shape memory disk-like optical element for affording the AIOL a natural positive diopter strength for near vision. The AIOL is intended to be implanted in a human eye such that relaxation of its ciliary body causes its capsular diaphragm to apply an accommodation force for overcoming the biasing mechanism to reduce the AIOL's natural positive diopter strength for distance vision.

8 Claims, 6 Drawing Sheets

U.S. PATENT DOCUMENTS

| | | |
|---|---|---|
| RE31,963 E | 8/1985 | Kelman |
| 4,556,998 A | 12/1985 | Siepser |
| 4,581,033 A | 4/1986 | Callahan |
| 4,589,147 A | 5/1986 | Nevyas |
| 4,591,358 A | 5/1986 | Kelman |
| 4,615,701 A | 10/1986 | Woods |
| 4,671,283 A | 6/1987 | Hoskin et al. |
| 4,676,794 A | 6/1987 | Kelman |
| 4,750,904 A | 6/1988 | Price, Jr. |
| 4,808,181 A | 2/1989 | Kelman |
| 4,842,601 A | 6/1989 | Smith |
| RE33,039 E | 8/1989 | Arnott |
| 4,865,601 A | 9/1989 | Caldwell et al. |
| 4,888,012 A | 12/1989 | Horn et al. |
| 4,892,543 A | 1/1990 | Turley |
| 4,932,966 A | 6/1990 | Christie et al. |
| 4,932,968 A | 6/1990 | Caldwell et al. |
| 4,957,505 A | 9/1990 | McDonald |
| 4,969,897 A | 11/1990 | Kalb |
| 4,976,732 A | 12/1990 | Vorosmarthy |
| 4,990,159 A | 2/1991 | Kraff |
| 5,078,742 A | 1/1992 | Dahan |
| 5,171,268 A | 12/1992 | Ting et al. |
| 5,176,701 A | 1/1993 | Dusek et al. |
| 5,275,623 A | 1/1994 | Sarfarazi |
| 5,282,851 A | 2/1994 | Jacob-LaBarre |
| 5,288,293 A | 2/1994 | O'Donnell |
| 5,336,262 A | 8/1994 | Chu |
| 5,346,502 A | 9/1994 | Estabrook et al. |
| 5,476,512 A | 12/1995 | Sarfarazi |
| 5,476,514 A | 12/1995 | Cumming |
| 5,476,515 A | 12/1995 | Kelman et al. |
| 5,480,426 A | 1/1996 | Chu |
| 5,484,447 A | 1/1996 | Waldock et al. |
| 5,489,302 A | 2/1996 | Skottun |
| 5,496,366 A | 3/1996 | Cumming |
| 5,522,891 A | 6/1996 | Klaas et al. |
| 5,567,365 A | 10/1996 | Weinschenk et al. |
| 5,571,177 A | 11/1996 | Deacon et al. |
| 5,607,472 A | 3/1997 | Thompson |
| 5,628,795 A | 5/1997 | Langerman |
| 5,674,282 A | 10/1997 | Cumming |
| 5,684,637 A | 11/1997 | Floyd |
| 5,722,952 A | 3/1998 | Schachar |
| 5,752,960 A | 5/1998 | Nallakrishnan |
| 5,766,244 A | 6/1998 | Binder et al. |
| 5,843,188 A | 12/1998 | McDonald |
| 5,871,455 A | 2/1999 | Ueno et al. |
| 5,919,230 A | 7/1999 | Sambursky |
| 5,968,094 A | 10/1999 | Werblin et al. |
| 6,007,579 A | 12/1999 | Lipshitz et al. |
| 6,051,024 A | 4/2000 | Cumming |
| 6,110,202 A | 8/2000 | Barraquer et al. |
| 6,117,171 A | 9/2000 | Skottun |
| 6,129,759 A | 10/2000 | Chambers |
| 6,164,282 A | 12/2000 | Gwon et al. |
| 6,193,750 B1 | 2/2001 | Cumming |
| 6,197,057 B1 | 3/2001 | Peyman et al. |
| 6,197,059 B1 | 3/2001 | Cumming |
| 6,200,342 B1 | 3/2001 | Tassignon et al. |
| 6,280,469 B1 | 8/2001 | Terry et al. |
| 6,280,471 B1 | 8/2001 | Peyman et al. |
| 6,299,618 B1 | 10/2001 | Sugiura |
| 6,299,641 B1 | 10/2001 | Woods |
| 6,342,073 B1 | 1/2002 | Cumming et al. |
| 6,387,126 B1 | 5/2002 | Cumming |
| 6,406,494 B1 | 6/2002 | Laguette et al. |
| 6,423,094 B1 | 7/2002 | Sarfarazi |
| 6,443,954 B1 | 9/2002 | Bramlet |
| 6,443,985 B1 | 9/2002 | Woods |
| 6,464,725 B2 | 10/2002 | Skottun |
| 6,488,708 B2 | 12/2002 | Sarfarazi |
| 6,494,910 B1 | 12/2002 | Ganem et al. |
| 6,494,911 B2 | 12/2002 | Cumming |
| 6,503,276 B2 | 1/2003 | Lang et al. |
| 6,506,212 B2 | 1/2003 | Zhou et al. |
| 6,520,691 B2 | 2/2003 | Nomura et al. |
| 6,554,860 B2 | 4/2003 | Hoffmann et al. |
| 6,570,718 B2 | 5/2003 | Nomura et al. |
| 6,596,026 B1 | 7/2003 | Gross et al. |
| 6,599,317 B1 | 7/2003 | Weinschenk, III et al. |
| 6,605,093 B1 | 8/2003 | Blake |
| 7,278,739 B2 | 8/2003 | Shadduck |
| 6,616,692 B1 | 9/2003 | Glick et al. |
| 6,638,305 B2 | 10/2003 | Laguette |
| 6,638,306 B2 | 10/2003 | Cumming |
| 6,645,245 B1 | 11/2003 | Preussner et al. |
| 6,739,722 B2 | 5/2004 | Laguette et al. |
| 6,749,634 B2 | 6/2004 | Hanna et al. |
| 6,790,232 B1 | 9/2004 | Lang |
| 6,849,091 B1 | 2/2005 | Cumming |
| 6,960,231 B2 | 11/2005 | Tran |
| 7,008,449 B2 | 3/2006 | Willis et al. |
| 7,037,338 B2 | 5/2006 | Nagamoto et al. |
| 7,097,660 B2 | 8/2006 | Portney |
| 7,118,597 B2 | 10/2006 | Miller et al. |
| 7,122,053 B2 | 10/2006 | Esch |
| 7,137,994 B2 | 11/2006 | De Juan, Jr. |
| 7,220,279 B2 | 5/2007 | Nun et al. |
| 7,261,737 B2 | 8/2007 | Esch et al. |
| 7,350,916 B2 | 4/2008 | Hong et al. |
| 2002/0103535 A1 | 8/2002 | Portney |
| 2002/0103537 A1 | 8/2002 | Willis et al. |
| 2003/0060881 A1 | 3/2003 | Glick et al. |
| 2003/0097177 A1 | 5/2003 | Tran |
| 2003/0109926 A1 | 6/2003 | Portney |
| 2003/0149480 A1 | 8/2003 | Shadduck |
| 2003/0199926 A1 | 10/2003 | Jensen |
| 2004/0073304 A1 | 4/2004 | Weinschenk, III et al. |
| 2004/0148022 A1 | 7/2004 | Eggleston |
| 2004/0169816 A1 | 9/2004 | Esch |
| 2005/0090896 A1 | 4/2005 | Ben Nun |
| 2005/0177229 A1 | 8/2005 | Boxer Wachle |
| 2006/0069433 A1 | 3/2006 | Nun |
| 2006/0074487 A1 | 4/2006 | Gilg |
| 2007/0027538 A1 | 2/2007 | Aharoni et al. |
| 2007/0088433 A1 | 4/2007 | Esch et al. |
| 2007/0129799 A1 | 6/2007 | Schedler |
| 2007/0185574 A1 | 8/2007 | Ben Nun |
| 2007/0244561 A1 | 10/2007 | Ben Nun |
| 2008/0004699 A1 | 1/2008 | Ben Nun |
| 2008/0188930 A1 | 8/2008 | Mentak et al. |
| 2009/0264998 A1 | 10/2009 | Mentak et al. |

FOREIGN PATENT DOCUMENTS

| | | |
|---|---|---|
| EP | 1321112 A | 6/2003 |
| FR | 2 794 965 | 12/2000 |
| JP | 2005007029 | 1/2005 |
| TW | 523408 | 3/2003 |
| WO | WO 83/00998 | 3/1983 |
| WO | WO 9428825 | 12/1994 |
| WO | WO-95/20367 | 8/1995 |
| WO | WO 98/05273 | 2/1998 |
| WO | WO 98/10717 | 3/1998 |
| WO | WO-99/62434 | 12/1999 |
| WO | WO-00/30566 | 6/2000 |
| WO | WO-00/61036 | 10/2000 |
| WO | WO-00/66037 | 11/2000 |
| WO | WO 01/08606 | 2/2001 |
| WO | WO-01/60286 | 8/2001 |
| WO | WO-02/065951 | 8/2002 |
| WO | WO 03/000154 | 1/2003 |
| WO | WO-03/015669 | 2/2003 |

| | | |
|---|---|---|
| WO | WO-2005/104994 | 11/2005 |
| WO | WO-2006/040759 | 4/2006 |
| WO | WO-2006/103674 | 10/2006 |
| WO | WO 2008/023379 | 2/2008 |
| WO | WO 2008/097915 | 8/2008 |
| WO | WO 2008/107882 | 9/2008 |
| WO | WO 2010/010565 | 1/2010 |

OTHER PUBLICATIONS

Chu, Ralph Y. and Buliano, Megan, Accommodating IOLs by Y. Ralph Cu et al, Cataract & Refractive Surgery Today, May 2004.

ACCOMMODATING INTRAOCULAR LENS (AIOL), AND AIOL ASSEMBLIES INCLUDING SAME

CROSS-REFERENCE TO RELATED APPLICATIONS

Domestic priority claim is made to U.S. Provisional Patent Application Ser. No. 60/617,738 filed on Oct. 13, 2004 and International priority claim is made to World Intellectual Property Organization (WIPO) PCT/IL2005/001069 filed on Oct. 9, 2005, assigned the International Publication Number WO 2006/040759 A1, published Apr. 20, 2006.

TECHNICAL FIELD

The invention pertains to accommodating intraocular lenses (AIOLs), and AIOL assemblies including same.

BACKGROUND OF THE INVENTION

Commonly owned PCT International Application No. PCT/IL02/00693 entitled Accommodating Lens Assembly and published under PCT International Publication No. WO 03/015669 illustrates and describes accommodating intraocular lens (hereinafter AIOL) assemblies, the contents of which are incorporated herein by reference. The AIOL assemblies include a haptics system adapted to be securely fixed in a human eye's annular ciliary sulcus at at least two spaced apart stationary anchor points so that it may act as a reference plane for an AIOL of continuously variable diopter strength affected by a human eye's capsular diaphragm acting thereagainst from a posterior direction and under the control of its sphincter-like ciliary body. WO 03/015669's FIGS. 1 and 2 show an AIOL assembly 2 designed to replicate a human eye's natural crystalline lens. The AIOL assembly 2 has a lens 6 made of a rigid material and a natural spherical shaped silicone ball 10 both having a refractive index greater than that of water. A human eye's capsular diaphragm directly bears against the silicone ball 10 from a posterior direction for resiliently elastically deforming it to a compressed flattened shape on relaxation of a human eye's ciliary body for decreasing its natural positive diopter strength for distance vision in a similar fashion to a human eye's natural crystalline lens. However, a human eye, and particularly an aging human eye, may be too weak to apply sufficient force to overcome such a silicone ball's inherent tendency to retain its natural shape thereby precluding accommodation.

Exemplary AIOLs are illustrated and described in U.S. Pat. No. 4,254,509 to Tennant, U.S. Pat. No. 4,409,691 to Levy, U.S. Pat. No. 4,888,012 to Horn et al., U.S. Pat. No. 4,892,543 to Turley, U.S. Pat. No. 4,932,966 to Christie et al., U.S. Pat. No. 5,476,514 to Cumming, U.S. Pat. No. 5,489,302 to Skottun, U.S. Pat. No. 5,496,366 to Cumming, U.S. Pat. No. 5,522,891 to Klaas, U.S. Pat. No. 5,674,282 to Cumming, U.S. Pat. No. 6,117,171 to Skottun, U.S. Pat. No. 6,197,059 to Cumming, U.S. Pat. No. 6,299,641 to Woods, U.S. Pat. No. 6,342,073 to Cumming et al., U.S. Pat. No. 6,387,126 to Cumming, U.S. Pat. No. 6,406,494 to Laguette et al., U.S. Pat. No. 6,423,094 to Sarfarazi, U.S. Pat. No. 6,443,985 to Woods, U.S. Pat. No. 6,464,725 to Skotton, U.S. Pat. No. 6,494,911 to Cumming, U.S. Pat. No. 6,503,276 to Lang et al., U.S. Pat. No. 6,638,306 to Cumming, U.S. Pat. No. 6,645,245 to Preussner, and US Patent Application Publication No. US 2004/0169816 to Esch.

BRIEF SUMMARY OF THE INVENTION

The present invention is for a novel AIOL including a biasing mechanism for elastically deforming an elastically deformable shape memory optical element for affording the AIOL with a natural positive diopter strength for near vision. The biasing mechanism is designed to apply a deforming force $F_{BM}$ bounded on its lower side to be marginally greater than a minimum deformation force $F_{OE}$ required to deform the optical element and on its upper side by the sum of the deformation force $F_{OE}$ and an accommodation force $F_{CD}$ effected by a human eye's capsular diaphragm in an anterior direction on relaxation of the human eye's ciliary body for enabling the optical element to revert to its natural shape to decrease the AIOL's natural positive diopter strength for distance vision. The forces acting on the optical element of the AIOL of the present invention can be mathematically expressed as $F_{OE}+F_{CD}>F_{BM}>F_{OE}$. By virtue of this arrangement, the AIOL of the present invention facilitates accommodation even in the case of an aging eye capable of applying an accommodation force $F_{CD}$ which may be considerably less than that of a healthy eye.

The AIOL forms part of an AIOL assembly intended for self-anchoring implantation in a human eye's ciliary sulcus at least two spaced apart stationary anchoring points. The AIOL can be mounted in a discrete haptics system enabling in situ displacement of the AIOL along a human eye's visual axis for enabling accurate eyesight correction in general, and for compensating for capsular contraction in particular. Alternatively, the AIOL can be integrally formed with a haptics system including plastically deformable haptics also enabling in situ AIOL displacement. Commonly owned PCT International Application No. PCT/IL2005/000456 entitled Accommodating Intraocular Lens Assemblies and Accommodation Measurement Implant illustrates and describes such a discrete haptics system, and a unitary construction including a haptics system with plastically deformable haptics and integrally formed with an AIOL both enabling in situ AIOL displacement, the contents of which are incorporated herein by reference.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF THE INVENTION

Figure 1:
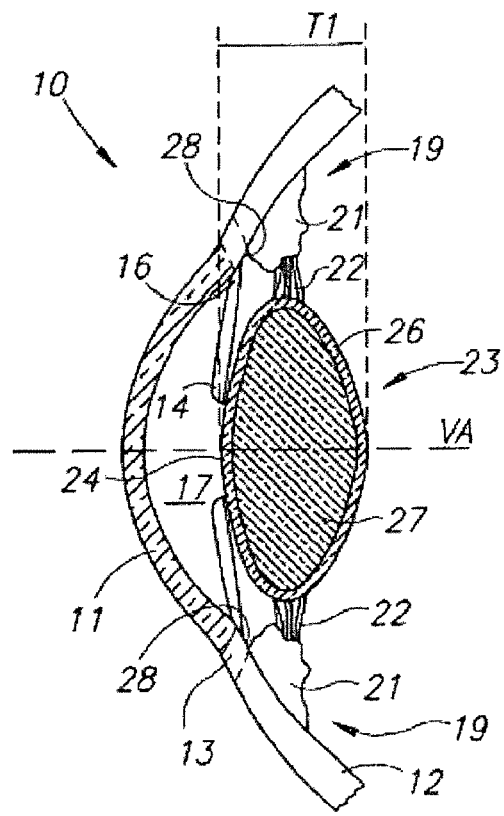
FIG. 1 is a cross section view of an anterior part of a human eye in its natural near vision condition in an axial plane of the human body.
Figure 2:
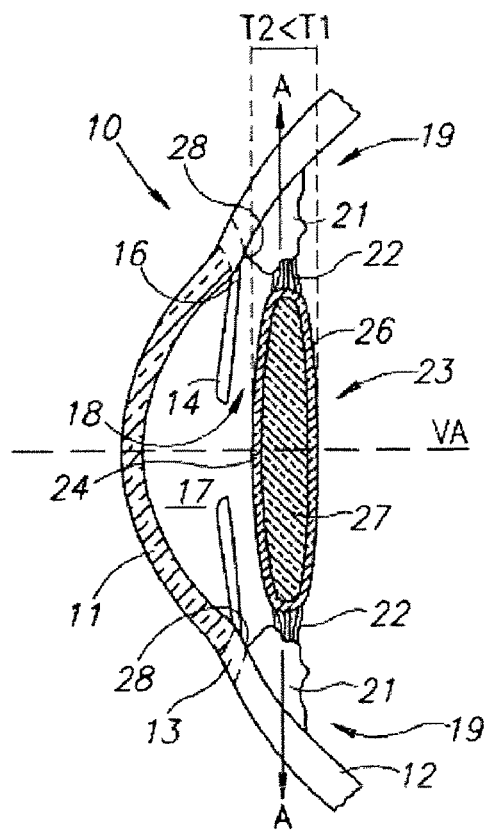
FIG. 2 is a cross section view of an anterior part of a human eye in its natural distance vision condition in an axial plane of the human body.

FIGS. 1 and 2 are cross sections of an anterior part of a human eye 10 having a visual axis VA in its natural near and distance vision conditions, respectively, in an axial plane of the human body. The human eye 10 has a cornea 11 peripherally connected to a spherical exterior body made of tough connective tissue known as the sclera 12 at an annular sclero-corneal juncture 13. An iris 14 inwardly extends into the human eye 10 from its root 16 at the sclero-corneal juncture 13 to divide the human eye's anterior part into an anterior chamber 17 and a posterior chamber 18. A sphincter-like peripheral structure known as the ciliary body 19 includes ciliary processes housing ciliary muscles 21 fired by parasympathetic nerves. The ciliary muscles 21 are connected to zonular fibers 22 which in turn are peripherally connected to the equatorial edge of a membrane known as the capsular bag 23 with an anterior capsule 24 and a posterior capsule 26 enrobing a natural crystalline lens 27. The iris's root 16 and the ciliary body 19 delimit a portion of the interior surface of the sclera 12 at the sclero-corneal juncture 13 known as the ciliary sulcus 28. Remnants of the anterior capsule 24 which may remain after extraction of the natural crystalline lens 27 and the intact posterior capsule 26 are referred to hereinafter as the capsular diaphragm 29. Contraction of the ciliary body 19 allows the lens 27 to thicken to its natural thickness T1 along the visual axis VA for greater positive optical power for near vision (see FIG. 1). Relaxation of the ciliary body 19 tensions the zonular fibers 22 which draws the capsular bag 23 radially outward as shown by arrows A for compressing the lens 27 to shorten its thickness along the visual axis VA to T2<T1 for lower positive optical power for distance vision (see FIG. 2).

Figure 3:
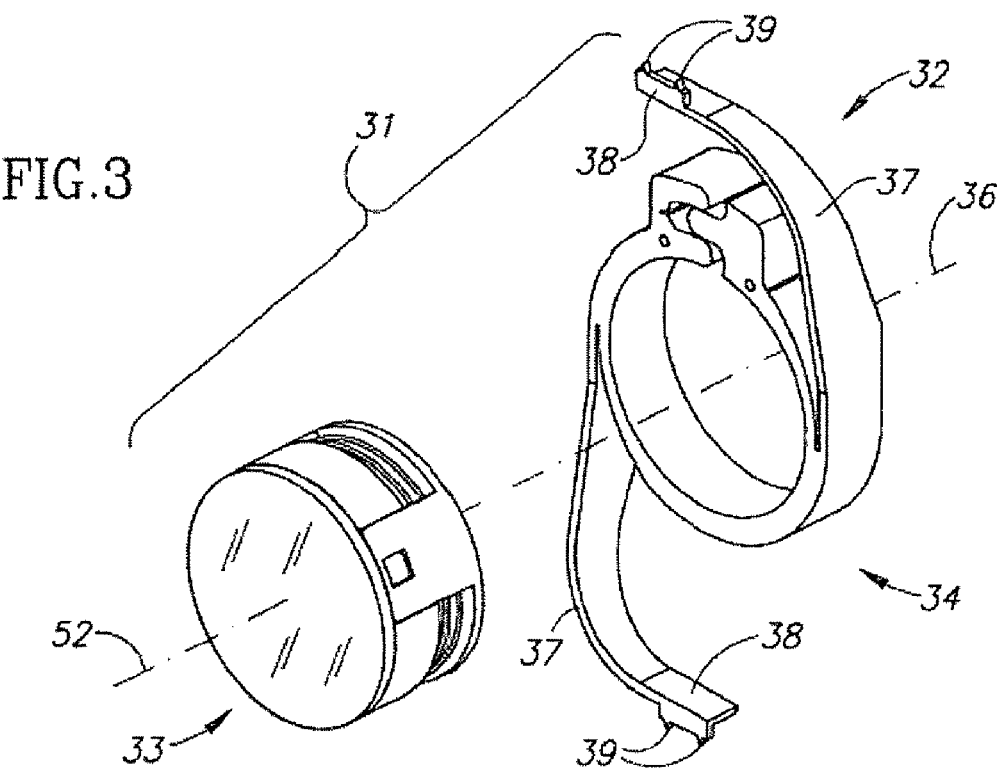
FIG. 3 is a perspective view of a dissembled two component AIOL assembly including a first preferred embodiment of an AIOL in accordance with the present invention.

FIG. 3 shows an AIOL assembly 31 for self-anchoring implantation in a human eye's ciliary sulcus 28 for enabling spectacle free vision over the nominal range of human vision. The AIOL assembly 31 includes a discrete haptics system 32 for selectively retaining a discrete AIOL 33 therein. The haptics system 32 is made from suitable bio-compatible material such as PMMA, and the like. The haptics system 32 includes a tubular main body 34 with a longitudinal axis 36 and an axial length L1 (see FIG. 6), and a pair of diametrically opposite haptics 37 tangentially extending therefrom in opposite directions in a front view of the haptics system 32. The haptics 37 have a pair of parallel and opposite attachment plates 38 with pointed penetrating members 39 of sufficient strength for forced penetration into the tough connective tissue of a human eye's sclera 12. The penetrating members 39 are preferably dimensioned so as to penetrate slightly more than half of a sclera's thickness of about 1 mm. Further details regarding the haptics system 32 are illustrated and described in the aforementioned PCT International Application No. PCT/IL2005/000456 in general, and FIGS. 3-5 in particular.

Figure 4:
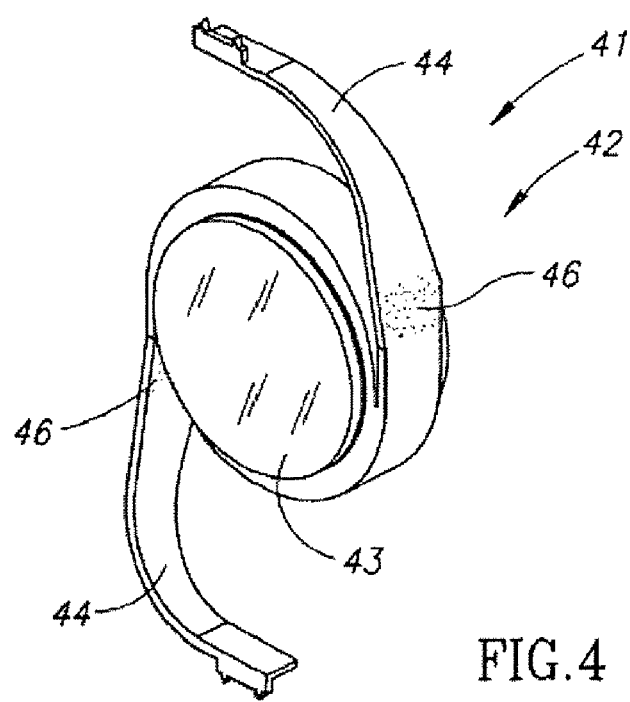
FIG. 4 is a perspective view of a unitary AIOL assembly integrally formed with a first preferred embodiment of an AIOL in accordance with the present invention.

FIG. 4 shows an AIOL assembly 41 for self-anchoring implantation in a human eye's ciliary sulcus 28 for enabling spectacle free vision over the nominal range of human vision. The AIOL assembly 41 includes a haptics system 42 integrally formed with an AIOL 43 similar in construction and operation as the discrete AIOL 33. The haptics system 42 is similar in construction as the haptics system 32 but differs therefrom insofar that it includes plastically deformable haptics 44 with regions 46 impregnated with radiation sensitive bio-compatible chemicals, for example, Infra Red (IR) sensitive indocyanine green (ICG), and the like, such that the haptics 44 are plastically deformable on heating to a so-called glass transition temperature. Further details regarding the haptics system 42 are illustrated and described in the aforementioned PCT International Application No. PCT/IL2005/000456 in general, and FIGS. 12-16 in particular.

Figure 5:
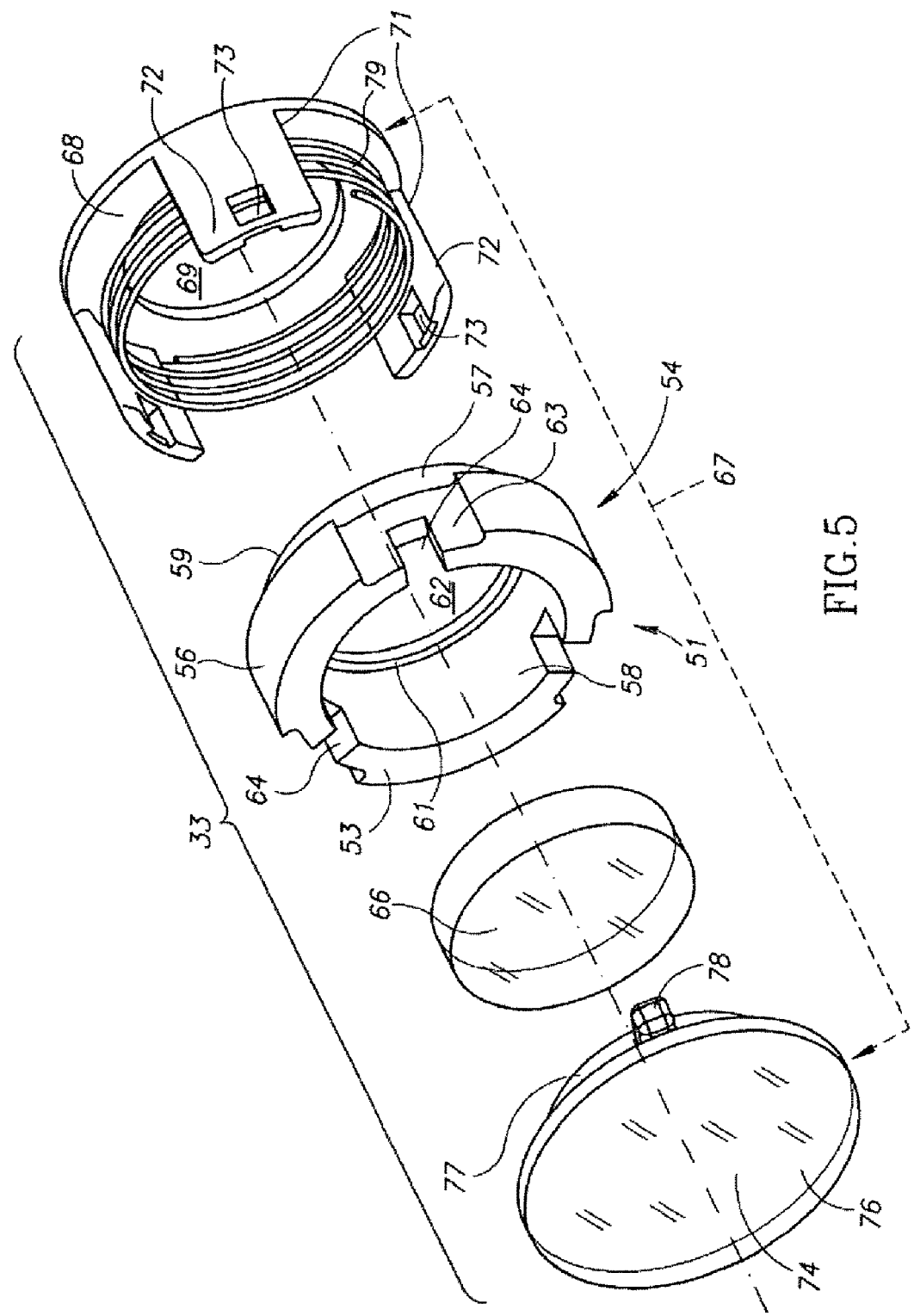
FIG. 5 is an exploded view of FIG. 3's AIOL.
Figure 6:
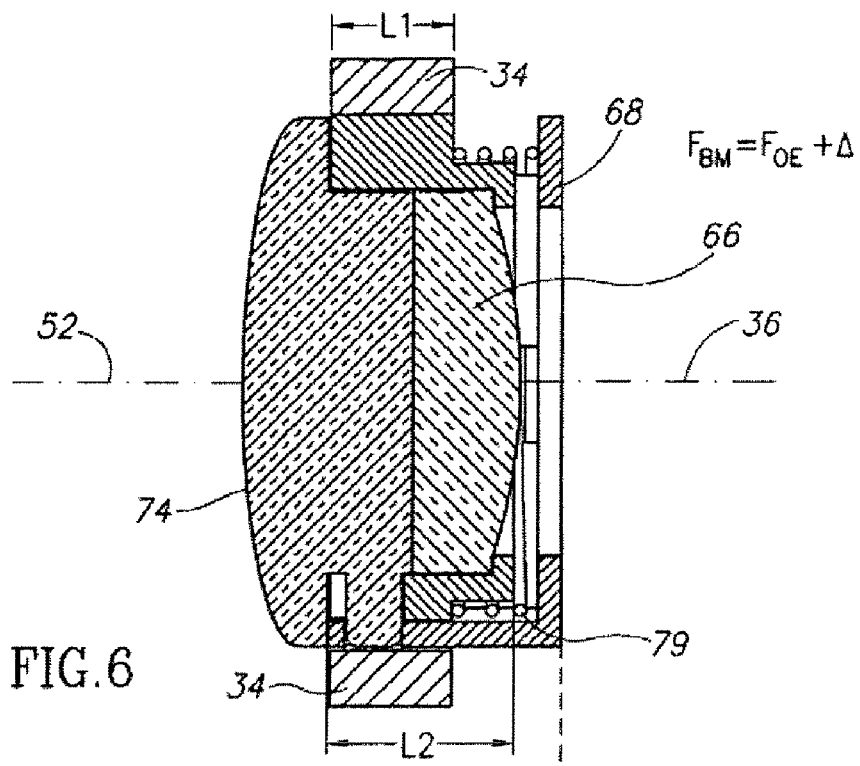
FIG. 6 is a longitudinal cross section of FIG. 3's AIOL in its near vision state.
Figure 7:
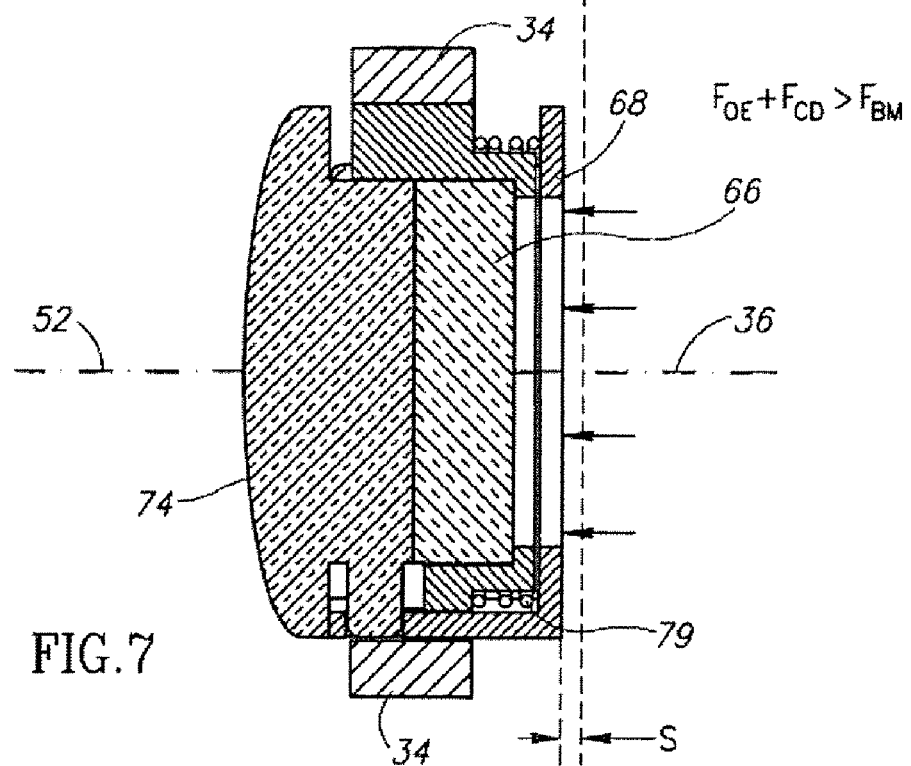
FIG. 7 is a longitudinal cross section of FIG. 3's AIOL in its distance vision state.

FIGS. 5-7 show the AIOL 33 includes a cup shaped casing 51 made from a suitable rigid bio-compatible material such as PMMA, and the like, and having an axial length L2 along a longitudinal axis 52, a leading surface 53, a stepped external surface 54 with a wide diameter leading portion 56 for secure clamping in the main body 34 and a narrow diameter trailing portion 57, a right cylindrical internal surface 58, and a trailing surface 59 formed with an annular flange 61 defining an aperture 62. The casing's axial length L2 is longer than the main body's axial length L1 such that the main body 34 is capable of contacting the casing 51 along an adjustment stroke longer than the main body's axial length L1. The leading portion 56 is formed with three peripherally disposed longitudinally directed grooves 63 formed with cutouts 64 in the leading surface 53. The casing 51 has a natural disc-like shape optical element 66 made of suitable elastically deformable bio-compatible material, such as, polymeric gel, hydrogel, and the like, having a refractive index greater than that of water. Suitable polymeric gels include silicone gel commercially available from NuSil Technology LLC., USA (www.nusil.com). The optical element 66 begins to undergo elastic deformation along its longitudinal axis on application of a minimum deformation force $F_{OE}$.

A rigid carriage 67 is slidingly mounted on the casing 51 from the exterior and includes an annular base plate 68 formed with an aperture 69 and three longitudinally directed struts 71 having free ends 72 each formed with an aperture 73, and an aperture lens 74 having a leading portion 76 and a trailing portion 77 formed with three equispaced radially directed protrusions 78 for snap fitting into the apertures 73. The base plate 68 is preferably formed from a suitable rigid bio-compatible material such as PMMA, and the like. The aperture lens 74 is preferably formed from a suitable rigid bio-compatible material such as PMMA, and the like. The aperture lens 74 preferably has sufficient positive diopter strength, say, in the range of between about +10 to about +30, for basic eyesight correction. The struts 71 are slidingly received in the grooves 63 such that the aperture lens 74 is lateral to the leading surface 53 and the base plate 68 is lateral to the trailing surface 59. The carriage 67 reciprocates through a stroke S between a first extreme position in which the base plate 68 is adjacent the trailing surface 59 and a second extreme position in which the base plate 68 is distanced from the trailing surface 59 relative to the first extreme position. A biasing mechanism 79 constituted by a compression spring is disposed between the trailing portion 57 and the struts 71 for urging the carriage 67 to its second extreme position. The biasing mechanism 79 applies a deforming force $F_{BM}$ where $F_{BM}=F_{OE}+\Delta$ for deforming the optical element 66 to bulge through the aperture 62 to afford the AIOL 33 with a positive diopter strength for near vision (see FIG. 6). The biasing mechanism 79 is designed such that an accommodation force $F_{CD}$ applied against the base plate 68 in an anterior direction on relaxation of the ciliary body 19 satisfies the condition that $F_{OE}+F_{CD}>F_{BM}$ such that the carriage 67 assumes its first extreme position for allowing the optical element 66 to revert to its natural disc-like shape to decrease the AIOL's natural positive diopter strength for distance vision (see FIG. 7).

Figure 8:
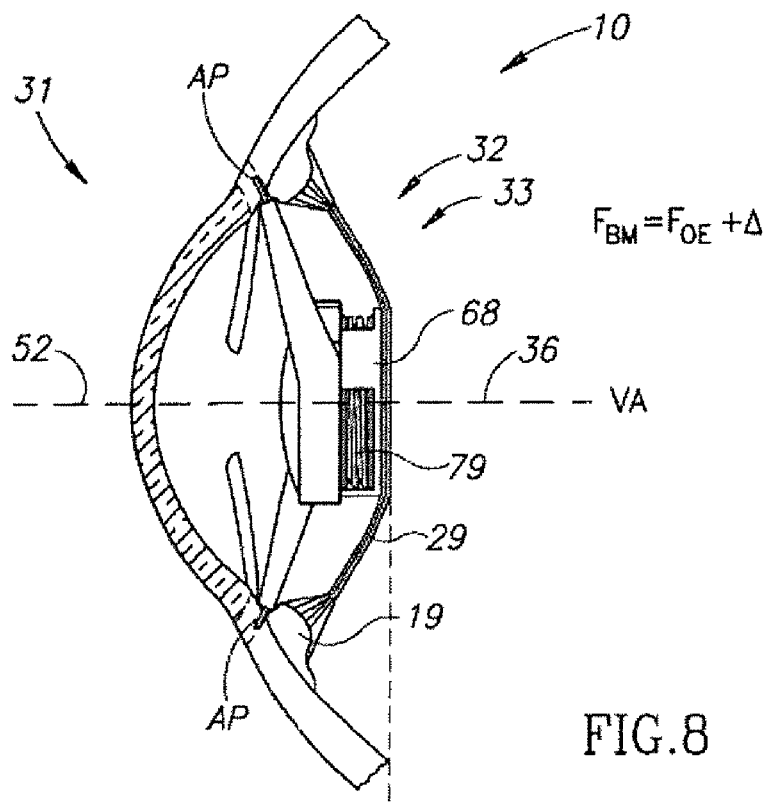
FIG. 8 is a cross section view of an anterior part of a human eye implanted with FIG. 3's AIOL in its near vision state in an axial plane of the human body.
Figure 9:
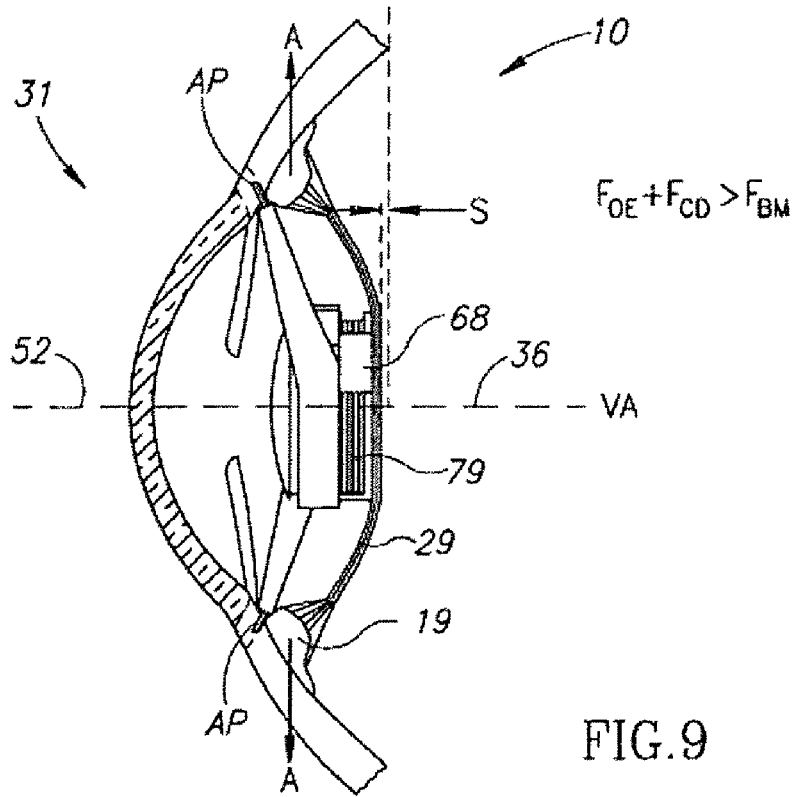
FIG. 9 is a cross section view of an anterior part of a human eye implanted with FIG. 3's AIOL in its distance vision state in an axial plane of the human body.

FIGS. 8 and 9 show the AIOL assembly 31 self-anchored in a human eye's ciliary sulcus at peripherally disposed stationary anchor points AP in its near vision and far distance states, respectively. The AIOL assembly 31 is implanted in a human eye 10 such that the capsular diaphragm 29 lightly bears against the base plate 68 in the contracted state of the human eye's ciliary body 19 such that on its relaxation, the capsular diaphragm 29 urges the AIOL 33 from its near vision state to its distance vision state.

Figure 10:
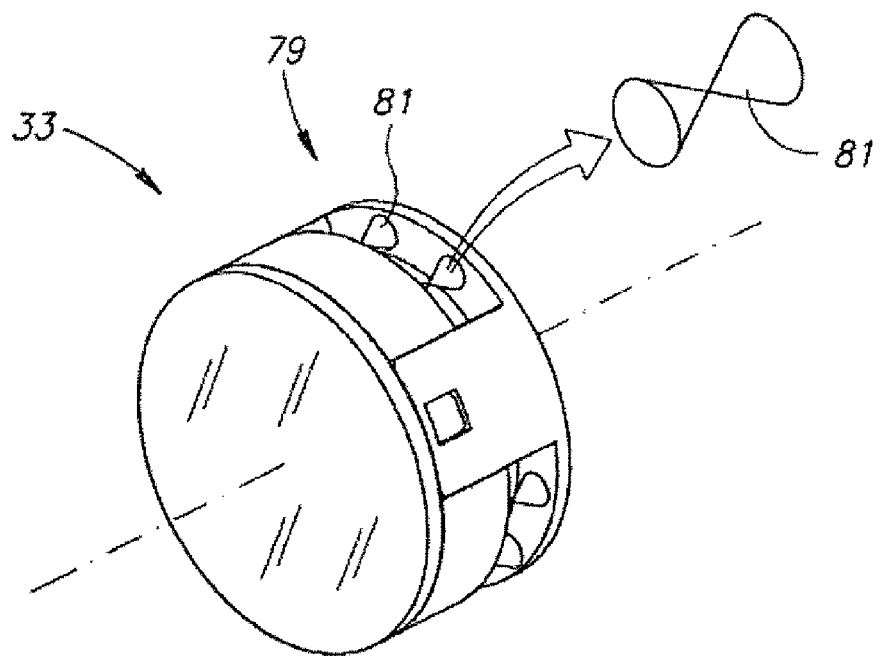
FIG. 10 is a perspective view of a second preferred embodiment of an AIOL in accordance with the present invention.
Figure 11:
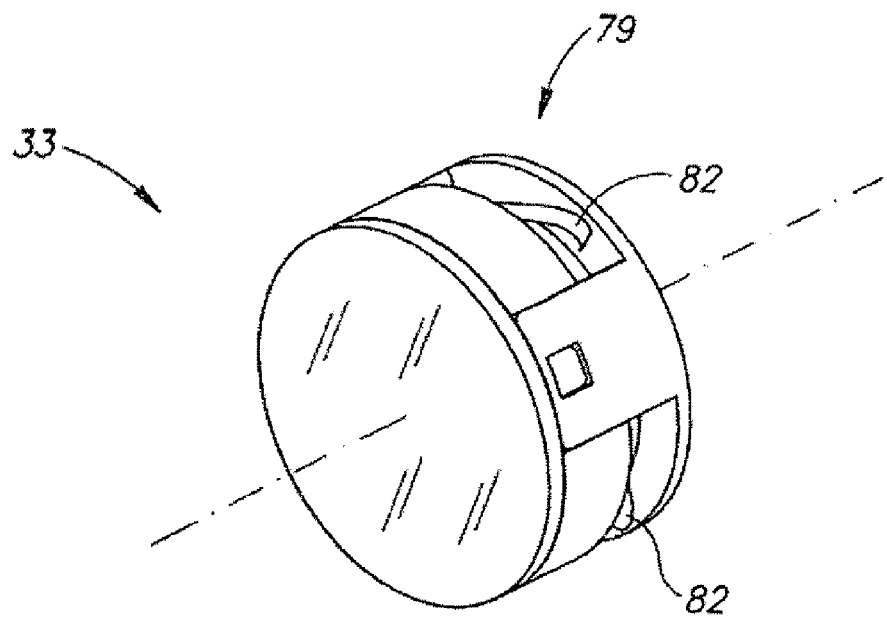
FIG. 11 is a perspective view of a third preferred embodiment of an AIOL in accordance with the present invention.

Although the present invention and its advantages have been described in detail, it should be understood that various changes, substitutions and alterations can be made herein without departing from the spirit and scope of the invention as defined by the appended claims. For example, the biasing mechanism 79 can be implemented by longitudinally compressible flex elements 81 (see FIG. 10), leaf springs 82 (see FIG. 11), and the like. Also, basic eyesight correction can be effected by a base plate instead of the aperture lens 74. Furthermore, the carriage can be assembled using non-mechanical techniques, for example, gluing, welding, and the like.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An accommodating intraocular lens (AIOL) comprising:
   (a) a cup shaped casing having a leading surface, a trailing surface with an aperture, and at least one elastically deformable shape memory optical element;
   (b) a carriage having a base plate and an aperture lens, and being slidingly mounted on said casing with said base plate lateral to said trailing surface for reciprocation between a first extreme position with said base plate adjacent said trailing surface and a second extreme position with said base plate distanced from said trailing surface relative to said first extreme position; and
   (c) a biasing mechanism for urging said carriage relative to said casing towards said second extreme position for deforming said at least one shape memory optical element to at least partially bulge through said aperture to afford the AIOL a natural positive diopter strength for near vision,
   said carriage being driven to said first extreme position on application of an external force to said base plate in an opposite direction to said urging direction to allow said at least one shape memory optical element to revert to its natural shape to decrease the AIOL's natural positive diopter strength for distance vision.

2. The AIOL according to claim 1 wherein said biasing mechanism is disposed between said trailing surface and said base plate.

3. The AIOL according to claim 2 wherein said biasing mechanism is a compression spring.

4. The AIOL according to claim 1 wherein said aperture lens has a diopter strength in the range of about +10 to about +30 for basic eyesight correction.

5. The AIOL according to claim 1 wherein said base plate is annular.

6. The AIOL according to claim 1 wherein said aperture lens is lateral to said leading surface.

7. The AIOL according to claim 1 wherein said carriage is externally mounted on said casing.

8. The AIOL according to claim 1 wherein said at least one shape memory optical element has a natural disc-like shape.

* * * * *